(12) United States Patent
Sode

(10) Patent No.: US 8,900,844 B2
(45) Date of Patent: Dec. 2, 2014

(54) GLUCOSE DEHYDROGENASE

(71) Applicants: ARKRAY, Inc., Kyoto (JP); Ultizyme International Ltd., Tokyo (JP)

(72) Inventor: Koji Sode, Tokyo (JP)

(73) Assignees: ARKRAY, Inc., Kyoto (JP); Ultizyme International Ltd., Tokyo (JP)

( * ) Notice: Subject to any disclaimer, the term of this patent is extended or adjusted under 35 U.S.C. 154(b) by 0 days.

(21) Appl. No.: 13/660,316

(22) Filed: Oct. 25, 2012

(65) Prior Publication Data

US 2013/0102016 A1     Apr. 25, 2013

Related U.S. Application Data

(62) Division of application No. 12/665,656, filed as application No. PCT/JP2008/001624 on Jun. 23, 2008, now Pat. No. 8,329,439.

(30) Foreign Application Priority Data

Jun. 21, 2007 (JP) .................................. 2007-163858

(51) Int. Cl.
| | |
|---|---|
| C12N 9/02 | (2006.01) |
| C12Q 1/54 | (2006.01) |
| C12Q 1/26 | (2006.01) |
| C07H 21/04 | (2006.01) |
| C12Q 1/00 | (2006.01) |
| C12N 9/04 | (2006.01) |

(52) U.S. Cl.
CPC ............... *C12N 9/0006* (2013.01); *C12Q 1/54* (2013.01); *C12Q 1/006* (2013.01); *C12Y 101/05002* (2013.01)
USPC ............... 435/189; 435/14; 435/25; 536/23.2

(58) Field of Classification Search
None
See application file for complete search history.

(56) References Cited

FOREIGN PATENT DOCUMENTS

| | | |
|---|---|---|
| JP | 2001-346587 A | 12/2001 |
| WO | 00/66744 A1 | 11/2000 |
| WO | 2004/005499 A1 | 1/2004 |
| WO | 2006/109578 A1 | 10/2006 |

OTHER PUBLICATIONS

International Search Report dated Aug. 12, 2008 issued in the international application No. PCT/JP2008/001624.
International Preliminary Report on Patentability dated Jan. 12, 2010 issued in the international application No. PCT/JP2008/001624.
Cleton-Jansen et al., "Cloning, characterization and DNA sequencing of the gene encoding the Mr 50000 quinoprotein glucose dehydrogenase from Acinetobacter calcoaceticus", Mol. Gen. Genet., 1989, vol. 217, pp. 430-436.
Oubrie et al., "The 1,7 Å crystal structure of the Apo Form of the Soluble Quinoprotein Glucose Dehydrogenase from Acinetobacter calcoaceticus reveals a novel internal conserved sequence repeat", J. Mol. Biol., 1999, vol. 289, pp. 319-333, and erratum.
Oubrie et al., "Structure and mechanism of soluble quinoprotein glucose dehydrogenase", The EMBO Journal, 1999, vol. 18, No. 19, pp. 5187-5194.
Oubrie et al., "Active-site structure of the soluble quinoprotein glucose dehydrogenase complexed with methylhydrazine: A covalent cofactor-inhibitor complex", PNAS, Oct. 12, 1999, vol. 96, No. 21, pp. 11787-11791.
Yagi, et al., "In silico panning for a non-competitive peptide inhibitor, BMC Bioinformatics", 2007, vol. 8, p. 11.
UniPro Accession No. A9EP27, created on Feb. 5, 2000.

*Primary Examiner* — Iqbal H Chowdhury
(74) *Attorney, Agent, or Firm* — Morgan, Lewis & Bockius LLP

(57) ABSTRACT

A modified pyrroloquinoline quinone glucose dehydrogenase that exhibits a high selectivity for glucose is provided. A modified pyrroloquinoline quinone glucose dehydrogenase is disclosed in which the amino acid residue G at Position 99 of a pyrroloquinoline quinone glucose dehydrogenase (PQQGDH) represented by SEQ ID NO: 1, or the amino acid residue G at Position 100 of the pyrroloquinoline quinone glucose dehydrogenase (PQQGDH) represented by SEQ ID NO: 3, is substituted by the amino acid sequence TGZN (where Z is SX, S, or N and X is any amino acid residue). The modified PQQGDH of the present invention may additionally comprise one or more mutations selected from the group consisting of Q192G, Q192A, or Q192S; L193X; E277X; A318X; Y367A, Y367F, or Y367W; G451C; and N452X (where X is any amino acid residue).

12 Claims, 1 Drawing Sheet

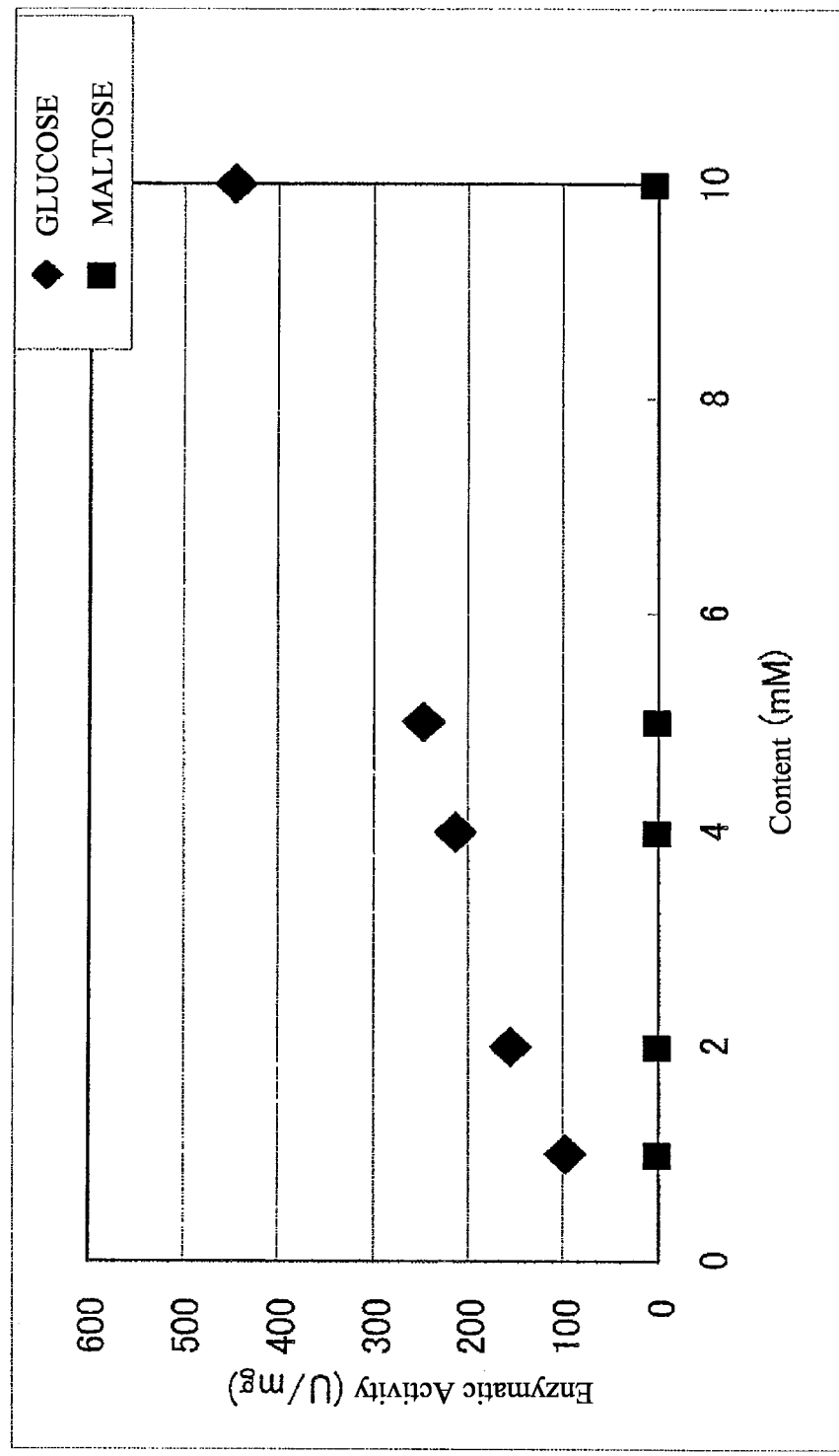

US 8,900,844 B2

GLUCOSE DEHYDROGENASE

TECHNICAL FIELD

The present application claims priority based on Japanese Patent Application No. 2007-163858 (filed 21 Jun. 2007), the contents of which are hereby incorporated by reference.

The present invention relates to a pyrroloquinoline quinone-dependent glucose dehydrogenase (PQQGDH) and to its preparation and use in the glucose assay.

BACKGROUND ART

The blood glucose level is an important marker for diabetes. The use of PQQGDH has already been commercialized as one method for measuring the glucose concentration.

PQQGDH is a glucose dehydrogenase that employs pyrroloquinoline quinone as a coenzyme, and it catalyses the oxidation of glucose with the production of gluconolactone. PQQGDH is known to occur as a membrane-bound enzyme and as a water-soluble enzyme. Membrane-bound PQQGDHs are single peptide proteins with molecular weights of approximately 87 kDa and are widely encountered in various Gram-negative bacteria. Water-soluble PQQGDH, on the other hand, has been identified in several strains of *Acinetobacter calcoaceticus*, and its structural gene was cloned and its amino acid sequence was determined (Gen-Bank accession number X15871; *Mol. Gen. Genet.* (1989), 217: 430-436). The results of X-ray crystal structural analysis of water-soluble PQQGDH from *Acinetobacter calcoaceticus* have been reported and the higher order structure of the enzyme, and most importantly the active center, has been elucidated. (A. Oubrie et al., *J. Mol. Biol.*, 289, 319-333 (1999); A. Oubrie et al., *The EMBO Journal*, 18(19), 5187-5194 (1999); A. Oubrie et al., *PNAS*, 96(21), 11787-11791 (1999)). Water-soluble PQQGDH from *Acinetobacter baumannii* has also been identified (GenBank accession number E28183).

PQQGDHs have a high oxidation activity for glucose and do not require oxygen as an electron acceptor because they are coenzyme-linked enzymes. As a result they are expected to find application in glucose assays and particularly as the recognition element of glucose sensors. A problem with PQQGDHs, however, is their low selectivity for glucose. In particular, PQQGDH also has a high activity for maltose, and thus accurate assay is difficult in patients receiving a maltose-containing infusion solution. In this case, the apparent blood sugar level will be higher than the actual blood sugar level, which could lead to a risk of hypoglycemia caused by administering insulin to the patient based on the measured level. Accordingly, a PQQGDH that exhibits a higher selectivity for glucose versus maltose is desired for the enzyme used for measurement of the blood sugar level.

The present inventor has already reported several modified PQQGDHs that exhibit an increased selectivity for glucose (for example, WO 00/66744, Japanese Patent Application Laid-open No. 2001-346587, and WO 2004/005499), but a modified PQQGDH that exhibits an even higher selectivity and/or an even higher enzymatic activity is still required.

The reference documents cited herein are listed below. The contents of these documents are hereby incorporated by reference in its entirety. None of these documents are admitted to constitute a prior art of the present invention.
Patent Document 1: WO 00/66744
Patent Document 2: Japanese Patent Application Laid-open No. 2001-346587
Patent Document 3: WO 2004/005499
Nonpatent Document 1: *Mol. Gen. Genet.* (1989), 217:430-436
Nonpatent Document 2: A. Oubrie et al. (1999) *J. Mol. Biol.*, 289, 319-333
Nonpatent Document 3: A. Oubrie et al. (1999) *The EMBO Journal*, 18(19), 5187-5194
Nonpatent Document 4: A. Oubrie et al. (1999) *PNAS*, 96(21), 11787-11791

DISCLOSURE OF THE INVENTION

An object of the present, invention is to provide a modified pyrroloquinoline quinone glucose dehydrogenase that exhibits a high selectivity for glucose.

The present inventor discovered that the selectivity for glucose is increased by the insertion, in a particular position in water-soluble PQQGDH, of a peptide fragment comprising 4 or 5 amino acids having a predetermined sequence.

The present invention provides a modified pyrroloquinoline quinone glucose dehydrogenase in which the amino acid residue G at Position 99 of a pyrroloquinoline quinone glucose dehydrogenase (PQQGDH) represented by SEQ ID NO: 1 or the amino acid residue G at Position 100 of the PQQGDH represented by SEQ ID NO: 3 is substituted by the amino acid sequence TGZN (where Z is SX, S, or N and X is any amino acid residue), and wherein from 1 to 10 of amino acid residues at Positions 1 to 98 and amino acid residues at Positions 100 to 478 of SEQ ID NO: 1, or amino acid residues at Positions 1 to 99 and amino acid residues at Positions 101 to 480 of SEQ ID NO: 3, may be substituted by any other amino acid residue(s). Z in the modified pyrroloquinoline quinone glucose dehydrogenase of the present invention is preferably SX and is particularly preferably SN.

Preferably, the modified pyrroloquinoline quinone glucose dehydrogenase of the present invention further comprises one or more mutations selected from the group consisting of the following amino acid substitutions:
Q192G, Q192A, or Q192S;
L193X (where X is any amino acid residue);
E277X (where X is any amino acid, residue);
A318X (where X is any amino acid residue);
Y367A, Y367F, or Y367W;
G451C; and
N452X (where X is any amino acid residue).

In another aspect the present invention provides a gene coding for the modified pyrroloquinoline quinone glucose dehydrogenase according to the present invention, a recombinant vector comprising the gene, and a transformant or transfectant that has been transformed with the recombinant vector. The present invention further provides a method of preparing the modified pyrroloquinoline quinone glucose dehydrogenase, comprising culturing a transformant that was transformed by a recombinant vector comprising a gene coding for the modified pyrroloquinoline quinone glucose dehydrogenase according to the present invention; and recovering the modified pyrroloquinoline quinone glucose dehydrogenase from the culture.

In an additional aspect the present invention provides a glucose assay kit comprising the modified pyrroloquinoline quinone glucose dehydrogenase according to the present invention. The present invention additionally provides an enzyme electrode comprising the modified pyrroloquinoline quinone glucose dehydrogenase according to the present invention, as well as a glucose sensor comprising this enzyme electrode as a working electrode.

The modified pyrroloquinoline quinone glucose dehydrogenase of the present invention exhibits a high selectivity for glucose as well as a high glucose oxidation activity, and can therefore be used for the highly selective and highly sensitive assay of glucose.

BRIEF DESCRIPTION OF THE DRAWINGS

FIG. 1 shows the enzymatic activity of the modified PQQGDH of the present invention for glucose and maltose.

PREFERRED EMBODIMENT OF THE INVENTION

Structure of the Modified PQQGDH

The modified pyrroloquinoline quinone glucose dehydrogenase of the present invention is characterized in that the amino acid residue G at Position 99 of the water-soluble PQQGDH shown by SEQ ID NO: 1 or the amino acid residue G at Position 100 of the PQQGDH shown by SEQ ID NO: 3 is substituted by the amino acid sequence TGZN (where z is SX, S, or N and X is any amino acid residue). As used herein, the position of an amino acid in the amino acid sequence of the water-soluble PQQGDHs is numbered by assigning 1 to the initiation methionine.

The PQQGDH represented by SEQ ID NO: 1 is a PQQGDH from *Acinetobacter calcoaceticus* (GenBank accession number X15871) and the PQQGDH represented by SEQ ID NO: 3 is a PQQGDH from *Acinetobacter baumannii* (GenBank accession number E28183). These PQQGDHs have an approximately 92% homology at the level of the amino acid sequence. The alignment of the two sequences is shown below.

These two PQQGDHs have similar secondary structures, and it is known that the properties of enzymes, for example, the thermal stability and substrate specificity, are similarly changed by the substitution of corresponding amino acid residues.

Z in the modified pyrroloquinoline quinone glucose dehydrogenase of the present invention is preferably SX and particularly preferably is SN. Thus, the amino acid sequence TGSXN, preferably TGSNN, and particularly preferably TGSKN, TGSRN, or TGSWN is inserted in place of the amino acid residue G at Position 99 in SEQ ID NO: 1 or in place of the amino acid residue G at Position 100 in SEQ ID NO: 3. TGSN or TGNN is also preferably inserted in place of this amino acid residue G.

The modified PQQGDH of the present invention has a higher selectivity for glucose than naturally occurring watersoluble PQQGDH. The modified PQQGDH of the present invention preferably has a lower reactivity for maltose versus reactivity for glucose than does the wild type. Given the reactivity for glucose is 100%, preferably the activity for maltose is not more than 50%, more preferably not snore than 30%, even more preferably not more than 20%, and most preferably not more than 10%.

The modified PQQGDH of the present invention may have other mutations in addition to the mutation in the amino acid residue at Position 99 of SEQ ID NO: 1 or at Position 100 of SEQ ID NO: 3. For example, one or more, for example, from 1 to 10, of the amino acid residues at Positions 1 to 98 or at Positions 100 to 478 of SEQ ID NO: 1, or the amino acid residues at Positions 1 to 99 or at Positions 101 to 480 of SEQ ID NO: 3, may be substituted by any other amino acid residue.

TABLE 1

```
_aln. pos       10        20        30        40        50        60
Calcoace   MNKHLLAKIALLSAVQLVTL-SAFADVPLTPSQFAKAKSENFDKKVILSNLNKPHALLWGPDNQIWLT  (SEQ ID NO: 1)
Baumannii  MNKHLLAKITLLGAAQLFTFHTAFADIPLTPAQFAKAKTENFDKKVILSNLNKPHALLWGPDNQIWLT  (SEQ ID NO: 3)
_consrvd   ************ * ** *     * **** ****** *****************************

_aln. p    70        80        90       100       110       120       130
calcoace   ERATGKILRVNPESGSVKTVFQVPEIVNDADGQNGLLGFAFHPDFKNNPYIYISGTFKNPKSTD
Baumannii  ERATGKILRVNPVSGSAKTVFQVPEIVSDADGQNGLLGFAFHPDFKHNPYIYISGTFKNPKSTD
_consrvd   ************ *** *********** ****************** ****************

_aln. pos   140       150       160       170       180       190       200
calcoace   KELPNQTIIRRYTYNKSTDTLEKPVDLLAGLPSSKDHQSGRLVIGPDQKIYYTIGDQGRNQLAYLFLP
Baumannii  KELPNQTIIRRYTYNKTTDTFEKPIDLIAGLPSSKDHQSGRLVIGPDQKIYYTIGDQGRNQLAYLFLS
_consrvd   **************** *** ** ** *************************************

_aln. pos   210       220       230       240       250       260       270
calcoace   NQAQHTPTQQELNGKDYHTYMGKVLRLNLDGSIPKDNPSFNGVVSHIYTLGHRNPQGLAFTPNGKLLQ
Baumannii  NQAQHTPTQQELNSKDYHTYMGKVLRLNLDGSIPKDNPSFNGVVSHIYTLGHRNPQGLAFAPNGKLLQ
_consrvd   ************* ********************************************* ********

_aln. pos   280       290       300       310       320       330       340
calcoace   SEQGPNSDDEINLIVKGGNYGWPNVAGYKDDSGYAYANYSAAANK-SIKDLAQNGVKVAAGVPVTKES
Baumannii  SEQGPNSDDEINLVLKGGNYGWPNVAGYKDDSGYAYANYSAATNKSQIKDLAQNGIKVATGVPVTKES
_consrvd   ************* *************************** **  ******** *** *******

_aln. pos   350       360       370       380       390       400
calcoace   EWTGKNFVPPLKTLYTVQDTYNYNDPTCGEMTYICWPTVAPSSAYVYKGGKKAITGWENTLLVPSLKR
Baumannii  EWTGKNFVPPLKTLYTVQDTYNYNDPTCGEMAYICWPTVAPSSAYVYTGGKKAIPGWENTLLVPSLKR
_consrvd   ******************************* ************** ****** ************

_aln. pos  410       420       430       440       450       460       470
calcoace   GVIFRIKLDPTYSTTYDDAVPMFKSNNRYRDVIASPDGNVLYVLTDTAGNVQKDDGSVTNTLENPGSL
Baumannii  GVIFRIKLDPTYSTTLDDAIPMFKSNNRYRDVIASPEGNTLYVLTDTAGNVQKDDGSVTHTLENPGSL
_consrvd   *************** *** ** **************** ** *********************** *******

_aln. pos  480
calcoace   IKFTYKAK
Baumannii  IKFTYNGK
_consrvd   ***** *
```

In a preferred embodiment of the present invention, the modified PQQGDH of the present invention has one or more mutations, preferably from 1 to 10 mutations, for example, 1, 2, 3, 4, 5, or 6 mutations, selected from the group consisting of
Q192G, Q192A, or Q192S;
L193X (where X is any amino acid residue);
E277X (where X is any amino acid residue);
A318X (where X is any amino acid residue);
Y367A, Y367F, or Y367W;
G451C; and
N452X (where X is any amino acid residue)
Wherein, the "Q192G" designation, for example, indicates that the glutamine at Position 192 in SEQ ID NO: 1, or the corresponding glutamine at Position 193 in SEQ ID NO: 3, is substituted by glycine. The other substitutional mutations are also indicated in the same manner.

A particularly preferred embodiment of the present invention is a modified pyrroloquinoline quinone glucose dehydrogenase comprising any of the following combinations of amino acid mutations:
G99(TGSXN)+Q192G+L193E;
G99(TGSXN)+Q192S+N452P;
G99(TGSXN)+Q192G+L193E*N452P;
G99(TGSXN)+Q192S+N452P;
G99(TGSNN)+N452P;
G99(TGSKN)+Q192G+L193E*N452P;
G99(TGSKN)+Q192S+N452P;
G99(TGSNN)+Q192G+N452P;
G99(TGSKN)+L193E+N452P;
G99(TGSNN)+Q192S+L193M+N452P;
G99(TGSNN)+A318Y+N452P;
G99(TGSNN)+Q192G;
G99(TGSKN)+Q192S;
G99(TGSNN)+Q192A;
G99(TGSNN)+Q192G+L193E;
G99(TGSKN)+Q192S+L193X;
G99(TGSKN)+Q192S+L193M;
G99(TGSNN)+Q192S+L193T;
G99(TGSKN)+Q192S+E277X;
G99(TGSKN)+Q192S+N452X;
G99(TGSNN)+Q192S+L193X+A313Y+N452P;
G99(TGSKN)+Q192S+A318X+N452P;
G99(TGSNN)+Q192G+L193E+A318X+N452P;
G99(TGSKN)+Q192S+N452P;
G99(TGSRN)+Q192S+N452P;
G99(TGSWN)+Q192S+N452P;
G99(TGSN)+Q192S+N452P;
G99(TGSN)+Q192G+L193E;
G99(TGSN)+Q192S+L193M;
G99(TGNN)+Q192S+N452P;
G99(TGNN)+Q192G+L193E; or
G99(TGNN)+Q192S+L193M.
Wherein X is any amino acid reside, for example, G99(TGSXN) indicates that the G at Position 99 in the PQQGDH represented by SEQ ID NO: 1 is substituted by TGSXN.

Another preferred embodiment of the present invention is a modified pyrroloquinoline quinone glucose dehydrogenase comprising any of the following amino acid mutations:
G99(TGSXN)+Q192G+L193E;
G99(TGSXN)+Q192S+N452P;
G99(TGSKN)+Q192G+L193E+N452P;
G99(TGSKN)+Q192S+L193M+N452P;
G99(TGSNN)+Q192G+L193E+A318K+N452P; or
G99(TGSKN)+Q192G+L193E+A318Q+N452P.

WO 04/005499 discloses that the glutamine residue at Position 192, the leucine residue at Position 193, and the asparagine residue at Position 452 are involved in substrate recognition and binding by PQQGDH. In general, however, it is completely unpredictable how the substrate specificity and enzymatic activity will change when mutations are simultaneously introduced in amino acid residues present in different domains. A complete loss of enzymatic activity may even occur in some cases. Accordingly, it was totally unpredictable if the selectivity for glucose would be further enhanced by the simultaneous introduction of the above-indicated substitutions and an insertion mutation at the amino acid residue at Position 99 in SEQ ID NO: 1 or the amino acid residue at Position 100 in SEQ ID NO: 3.

Method of Producing Modified PQQGDH

The sequence of the gene coding for naturally occurring water-soluble PQQGDH from *Acinetobacter calcoaceticus* is shown in SEQ ID NO: 2, while the sequence of the gene coding for naturally occurring water-soluble PQQGDH from *Acinetobacter baumannii* is shown in SEQ ID NO:4. A gene coding for the modified PQQGDH of the present invention can be constructed by replacing the nucleotide sequence coding for the amino acid residue targeted for substitution in the gene coding for naturally occurring water-soluble PQQGDH with a nucleotide sequence coding for the desired amino acid residue. Methods for such a site-specific sequence substitution are well known in the art; for example, by PCR using suitably designed primers, as is described in the examples provided below.

The thus obtained mutant gene is inserted in an expression vector (for example, a plasmid), which is then transformed into a suitable host (for example, *E. coli*). A large number of vector/host systems for the expression of foreign protein are known in the art. A variety of hosts, for example, bacteria, yeast, cultured cells, and so forth are available.

In addition, a portion of other amino acid residues in the modified PQQGDH of the present invention may also be deleted or substituted, and other amino acid residues may be added, insofar as it has a desired, glucose dehydrogenase activity. Various methods for site-specific nucleotide sequence substitution are well known in the art.

The modified PQQGDH-expressing transformant obtained as described above is then cultured, and the cells are recovered from the culture fluid by, for example, centrifugation. The recombinant, protein present in vhe periplasmic compartment is subsequently released into culture medium, by grinding the cells, for example, with a French press, or by osmotic shock. Ultracentrifugation is thereafter carried out to obtain a water-soluble fraction containing the modified PQQGDH. Alternatively, through the use of a suitable host-vector system, the expressed modified PQQGDH can be secreted into the culture fluid. The modified PQQGDH of the present invention can be isolated by purifying the water-soluble fraction by, for example, ion-exchange chromatography, affinity chromatography, HPLC, and so forth.

Method of Measuring the Enzymatic Activity

The modified PQQGDH of the present invention has the ability to catalyze the oxidation of glucose with PQQ as its coenzyme, with the production of gluconolactone. To measure the enzymatic activity, the quantity of PQQ that is reduced accompanying the PQQGDH-mediated glucose oxidation can be quantitated by the color reaction of a redox dye. For example, phenazine methosulfate (PMS), 2,6-dichlorophenolindophenol (DCIP), potassium ferricyanide, ferrocene, and so forth, can be used as the chromogenic reagent.

Selectivity for Glucose

The selectivity for glucose exhibited by the modified PQQGDH of the present invention can be evaluated by measuring the enzymatic activity in the manner described above using various sugars as substrates, e.g., 2-deoxy-D-glucose, mannose, allose, 3-o-methyl-D-glucose, galactose, xylose, lactose, maltose, and so forth, and determining the relative activity with reference to the activity using glucose as the substrate.

The modified PQQGDH of the present invention provides a higher selectivity for glucose than the wild-type enzyme and in particular has a higher reactivity for glucose than for maltose. Accordingly, an assay kit or enzyme sensor constructed using the modified PQQGDH of the present invention will exhibit a high selectivity with regard to glucose measurement and offers the advantage of high-sensitivity glucose detection even when a maltose-containing sample is used.

Glucose Assay Kit

Another aspect of the present invention is a glucose assay kit comprising a modified PQQGDH according to the present invention. The glucose assay kit of the present invention comprises the modified PQQGDH according to the present invention in a quantity sufficient for conducting at least one assay. In addition to the modified PQQGDH of the present invention, the kit will typically comprise a buffer required for the assay, a mediator, a glucose reference solution for constructing a calibration curve, and instructions for use. The modified PQQGDH according to the present invention can be provided in various forms, for example, as a freeze-dried reagent or as a solution in a suitable storage solution. The modified PQQGDH of the present invention is preferably provided in a form of holoenzyme, but can also be provided as the apoenzyme and then converted into the holoenzyme before use.

Glucose Sensor

Additional aspect of the present invention is an enzyme electrode that carries a modified PQQGDH according to the present invention, and a glucose sensor comprising the enzyme electrode. For example, a carbon electrode, gold electrode, or platinum electrode can be used as the electrode, and the enzyme according to the present invention is immobilized on the electrode. The immobilization method can be exemplified by the use of a crosslinking reagent; enclosure in a polymer matrix; coating with a dialysis film; use of a photocrosslinking polymer, electroconductive polymer, or redox polymer; immobilization in a polymer or adsorptive immobilization on the electrode together with an electron mediator such as ferrocene and its derivatives; and the use of combinations of the preceding. The modified PQQGDH of the present invention is preferably immobilized on the electrode in a holoenzyme form, but can also be immobilized in an apoenzyme form with the PQQ being provided in a separate layer or in a solution. Typically, the modified PQQGDH of the present invention is immobilized on a carbon electrode via glutaraldehyde followed by treatment with an amine group-containing reagent to block the aldehyde groups of glutaraldehyde.

Measurement of the glucose concentration can be carried out as follows. Buffer solution is introduced into a thermostatted cell; PQQ, $CaCl_2$, and a mediator are added; and the cell is held at a constant temperature. Potassium ferricyanide, phenazine methosulfate, and so forth, may be used as the mediator. An electrode bearing the immobilized modified PQQGDH of the present invention is used as the working electrode, in combination with a counterelectrode (for example, a platinum electrode) and a reference electrode (for example, the Ag/AgCl electrode). A constant voltage is applied to the carbon electrode, and after the current becomes constant, a glucose-containing sample is added and the increase in the current is measured. The glucose concentration in the sample can be determined using a calibration curve constructed using glucose solutions of standard concentrations.

The contents of all the patents and reference documents explicitly cited herein are hereby incorporated by reference in its entirety.

The present invention is described in detail based on the following examples, but is not limited to these examples.

EXAMPLE 1

Construction of Modified PQQGDH-Encoding Genes

Mutation was introduced into the structural gene for water-soluble PQQGDH from *Acinetobacter calcoaceticus*, which is represented by SEQ ID NO: 2. In brief, PCR was carried out using a full length forward primer for the wild-type water-soluble PQQGDH and a mutagenic reverse primer, and another PCR was carried out using a full length reverse primer and a mutagenic forward primer. These PCR products were mixed and PCR was run using a full length forward primer and reverse primer to obtain a gene coding for the mutated full length PQQGDH. The product was sequenced to conform that the desired mutation was correctly introduced.

The sequence of the primers for full length amplification were as follows.

forward: AACAGACCATGGATAAACATTTATTGGC (SEQ ID NO: 5)

reverse: ACAGCCAAGCTTTTACTTAGCCTTATAGG (SEQ ID NO: 6)

The sequences of the mutagenic primers (F: forward, R: reverse) are shown in the following table.

TABLE 2

| Mutation | Primer Sequence | | SEQ ID NO |
|---|---|---|---|
| TGNN | ACTGGAAATAATCAGAATGGTTTATTAGGTTTT | F | 7 |
| | CTGATTATTTCCAGTATCAGCATCATTGACAAT | R | 8 |
| TGQN | ACTGGACAGAATCAGAATGGTTTATTAGGTTTT | F | 9 |
| | CTGATTCTGTCCAGTATCAGCATCATTGACAAT | R | 10 |
| TGSN | ACTGGAAGCAATCAGAATGGTTTATTAGGTTTT | F | 11 |
| | CTGATTGCTTCCAGTATCAGCATCATTGACAAT | R | 12 |
| TGGN | ACTGGAGGTAATCAGAATGGTTTATTAGGTTTT | F | 13 |
| | CTGATTACCTCCAGTATCAGCATCATTGACAAT | R | 14 |
| TGSSN | GATACTGGAAGCAGCAATCAGAATGGTTTATTA | F | 15 |
| | ATTGCTGCTTCCAGTATCAGCATCATTGACAAT | R | 16 |
| TGWN | ACTGGATGGAATCAGAATGGTTTATTAGGTTTT | F | 17 |
| | CTGATTCCATCCAGTATCAGCATCATTGACAAT | R | 18 |
| TGFN | ACTGGATTTAATCAGAATGGTTTATTAGGTTTT | F | 19 |
| | CTGATTAAATCCAGTATCAGCATCATTGACAAT | R | 20 |
| TGDN | ACTGGAGATAATCAGAATGGTTTATTAGGTTTT | F | 21 |
| | CTGATTATCTCCAGTATCAGCATCATTGACAAT | R | 22 |
| TGSHN | GATACTGGAAGCCATAATCAGAATGGTTTATTA | F | 23 |
| | ATTATGGCTTCCAGTATCAGCATCATTGACAAT | R | 24 |
| TGSLN | GATACTGGAAGCTTAAATCAGAATGGTTTATTA | F | 25 |
| | ATTTAAGCTTCCAGTATCAGCATCATTGACAAT | R | 26 |
| TGSVN | GATACTGGAAGCGTCAATCAGAATGGTTTATTA | F | 27 |
| | ATTGACGCTTCCAGTATCAGCATCATTGACAAT | R | 28 |
| TGSQN | GATACTGGAAGCCAAAATCAGAATGGTTTATTA | F | 29 |
| | ATTTTGGCTTCCAGTATCAGCATCATTGACAAT | R | 30 |

TABLE 2 -continued

| Muta-tion | Primer Sequence | | SEQ ID NO |
|---|---|---|---|
| TGSEN | GATACTGGAAGCGAAAATCAGAATGGTTTATTA | F | 31 |
| | ATTTTCGCTTCCAGTATCAGCATCATTGACAAT | R | 32 |
| TGSDN | GATACTGGAAGCGATAATCAGAATGGTTTATTA | F | 33 |
| | ATTATCGCTTCCAGTATCAGCATCATTGACAAT | R | 34 |
| TGSPN | GATACTGGAAGCCCTAATCAGAATGGTTTATTA | F | 35 |
| | ATTAGGGCTTCCAGTATCAGCATCATTGACAAT | R | 36 |
| TGSTN | GATACTGGAAGCACAAATCAGAATGGTTTATTA | F | 37 |
| | ATTTGTGCTTCCAGTATCAGCATCATTGACAAT | R | 38 |
| TGSIN | GATACTGGAAGCATTAATCAGAATGGTTTATTA | F | 39 |
| | ATTAATGCTTCCAGTATCAGCATCATTGACAAT | R | 40 |
| TGSAN | GATACTGGAAGCGCTAATCAGAATGGTTTATTA | F | 41 |
| | ATTAGCGCTTCCAGTATCAGCATCATTGACAAT | R | 42 |
| TGSWN | GATACTGGAAGCTGGAATCAGAATGGTTTATTA | F | 43 |
| | ATTCCAGCTTCCAGTATCAGCATCATTGACAAT | R | 44 |
| TGSGN | GATACTGGAAGCGGTAATCAGAATGGTTTATTA | F | 45 |
| | ATTACCGCTTCCAGTATCAGCATCATTGACAAT | R | 46 |
| TGSFN | GATACTGGAAGCTTTAATCAGAATGGTTTATTA | F | 47 |
| | ATTAAAGCTTCCAGTATCAGCATCATTGACAAT | R | 48 |
| TGSYN | GATACTGGAAGCTATAATCAGAATGGTTTATTA | F | 49 |
| | ATTATAGCTTCCAGTATCAGCATCATTGACAAT | R | 50 |
| TGSCN | GATACTGGAAGCTGCAATCAGAATGGTTTATTA | F | 51 |
| | ATTGCAGCTTCCAGTATCAGCATCATTGACAAT | R | 52 |
| TGSMN | GATACTGGAAGCATGAATCAGAATGGTTTATTA | F | 53 |
| | ATTCATGCTTCCAGTATCAGCATCATTGACAAT | R | 54 |
| TGSKN | GATACTGGAAGCAAAAATCAGAATGGTTTATTA | F | 55 |
| | ATTTTTGCTTCCAGTATCAGCATCATTGACAAT | R | 56 |
| TGSRN | GATACTGGAAGCCGTAATCAGAATGGTTTATTA | F | 57 |
| | ATTACGGCTTCCAGTATCAGCATCATTGACAAT | R | 58 |
| TGSNN | GATACTGGAAGCAATAATCAGAATGGTTTATTA | F | 59 |
| | ATTATTGCTTCCAGTATCAGCATCATTGACAAT | R | 60 |

Other substitutional mutations, e.g., mutations such as Q192G and L193E were introduced using conventional site-specific mutagenesis methods as described in WO 00/66744. In addition, modified PQQGDHs that incorporated a combination of mutations at a plurality of sites were prepared by site-specific mutagenesis using a plurality of primers that corresponded to the individual mutations or were prepared by a recombinant method using restriction enzymes.

EXAMPLE 2

Production of Modified PQQGDH

The gene coding for wild-type PQQGDH or the gene coding for the modified PQQGDH constructed as described above was inserted in the multicloning site of an *E. coli* expression vector pTrc99A (Pharmacia), and the constructed plasmid was transformed into *E. coli*. The transformant was cultured with shaking overnight at 37° C. in 450 mL L-broth containing 50 μg/mL ampicillin and 30 μg/mL chloramphenicol. The culture was inoculated into 7 L of L-broth containing 1 mM CaCl$_2$ and 500 μM PQQ. At approximately 3 hours after the start of cultivation, isopropylthiogalactoside was added at a final concentration of 0.3 mM and continued cultivation for 1.5 hours. The cells were recovered from the culture medium by centrifugation (5000×g, 10 minutes, 4° C.) and suspended in 150 μL 10 mM MOPS (pH 7.0). Glass beads (0.105 to 0.125 mm for bacteria) were added in an amount that was ½ to ⅔ of the volume and vortexed for 20 minutes at 4° C. 1 mL 10 mM MOPS (pH 7.0) was added, and centrifuged (15,000 rpm, 20 minutes, 4° C.). The supernatant, was collected and used as a crude enzyme preparation in the following examples.

EXAMPLE 3

Measurement, of the Enzymatic Activity

900 μL of a mixture of 10 mM MOPS (pH 7.0)+1 mM PQQ+1 mM CaCl$_2$ holoenzyme conversion solution was added to 100 μL of the crude enzyme preparation of the wild-type PQQGDH or the modified PQQGDH obtained in Example 2 and left stand (room temperature, in the dark, at least 30 minutes) to allow for conversion to the holoenzyme. After completion of conversion to the holoenzyme, the solution was diluted 10× to prepare an enzyme test solution. To 150 μL of the enzyme test solution was added 50 μL of a given concentration of the substrate (glucose or maltose), 0.6 mM phenazine methosulfate (PMS), and 0.3 mM 2,6-dichlorophenolindophenol (DCIP, final concentrations in each case), and incubated at room temperature in the total volume of 200 μL. Glucose and maltose were used as the substrates at final concentrations of 0, 1, 2, 4, 10, 20, and 40 mM. The change in the DCIP absorbance at 600 nm was monitored with a spectrophotometer. The rate of decline in the absorbance was measured to determine the reaction rate of the enzyme. In the experiments described herein, 1 unit was designated as the enzymatic activity that reduces 1 μmol of DCIP in 1 minute with the molar absorption coefficient of 16.3 mM$^{-1}$ of DCIP at pH 7.0. The protein concentration was measured using a commercially available protein assay kit (BioRad).

Typical results are given in the following tables indicated by the ratio (%) of the activity for 4 mM maltose with reference to the activity for 4 mM glucose.

TABLE 3

| TGSXN | |
|---|---|
| Wild Type | 79 |
| Q192G + L193E | 9.0 |
| TGSAN | 54 |
| TGSCN | 47 |
| TGSDN | 60 |
| TGSEN | 51 |
| TGSGN | 52 |
| TGSHN | 46 |
| TGSIN | 42 |
| TGSKN | 43 |
| TGSMN | 43 |
| TGSNN | 42 |
| TGSPN | 47 |
| TGSQN | 42 |
| TGSRN | 43 |
| TGSSN | 57 |
| TGSTN | 47 |
| TGSVN | 39 |
| TGSWN | 33 |
| TGSFN | 58 |
| TGSLN | 49 |
| TGSYN | 63 |

TABLE 4

| TGSXN + Q192G + L193E | |
|---|---|
| Wild Type | 79 |
| Q192G + L193E | 9.0 |
| TGSGN + Q192G + L193E | 6.7 |
| TGSMN + Q192G + L193E | 5.7 |
| TGSNN + Q192G + L193E | 4.2 |
| TGSPN + Q192G + L193E | 6.6 |
| TGSQN + Q192G + L193E | 5.2 |
| TGSRN + Q192G + L193E | 6.0 |
| TGSSN + Q192G + L193E | 9.3 |
| TGSTN + Q192G + L193E | 7.4 |
| TGSVN + Q192G + L193E | 6.9 |
| TGSAN + Q192G + L193E | 15 |
| TGSDN + Q192G + L193E | 16 |
| TGSEN + Q192G + L193E | 20 |
| TGSHN + Q192G + L193E | 9.8 |
| TGSIN + Q192G + L193E | 20 |
| TGSKN + Q192G + L193E | 5.7 |
| TGSCN + Q192G + L193E | 17 |
| TGSWN + Q192G + L193E | 7.6 |

TABLE 5

| TGSNN + Q192S + E277X | |
|---|---|
| TGSNN + Q192S | 12 |
| TGSNN + Q192S + E277A | 20 |
| TGSNN + Q192S + E277D | 26 |
| TGSNN + Q192S + E277I | 15 |
| TGSNN + Q192S + E277T | 22 |
| TGSNN + Q192S + E277Q | 16 |
| TGSNN + Q192S + E277V | 23 |
| TGSNN + Q192S + E277W | 38 |
| TGSNN + Q192S + E277Y | 27 |
| TGSNN + Q192S + E277C | 12 |
| TGSNN + Q192S + E277F | 66 |
| TGSNN + Q192S + E277G | 34 |
| TGSNN + Q192S + E277H | 39 |
| TGSNN + Q192S + E277K | 29 |
| TGSNN + Q192S + E277L | 76 |
| TGSNN + Q192S + E277M | 64 |
| TGSNN + Q192S + E277N | 56 |
| TGSNN + Q192S + E277S | 13 |
| TGSNN + Q192S + E277R | 24 |
| TGSNN + Q192S + E277P | 39 |

TABLE 6

| TGSNN + Q192S + N452X | |
|---|---|
| TGSNN + Q192S + N452A | 8.9 |
| TGSNN + Q192S + N452C | 12 |
| TGSNN + Q192S + N452D | 20 |
| TGSNN + Q192S + N452E | nd |
| TGSNN + Q192S + N452F | 10 |
| TGSNN + Q192S + N452G | 14 |
| TGSNN + Q192S + N452H | 13 |
| TGSNN + Q192S + N452I | 14 |
| TGSNN + Q192S + N452K | 18 |
| TGSNN + Q192S + N452L | 7.8 |
| TGSNN + Q192S + N452M | 11 |
| TGSNN + Q192S + N452P | 1.9 |
| TGSNN + Q192S + N452Q | nd |
| TGSNN + Q192S + N452R | 27 |
| TGSNN + Q192S + N452S | 11 |
| TGSNN + Q192S + N452T | 14 |
| TGSNN + Q192S + N452V | 8.8 |
| TGSNN + Q192S + N452W | 79 |
| TGSNN + Q192S + N452Y | 9.3 |

TABLE 7

| TGSNN + Q192G/S/A | |
|---|---|
| Wild Type | 79 |
| Q192G + L193E | 9.0 |
| TGSNN + Q192G + L193E | 4.2 |
| Q192G | 20 |
| TGSNN + Q192G | 9.1 |
| Q192A | 15 |
| TGSNN + Q192A | 7.8 |
| Q192S | 28 |
| TGSNN + Q192S | 12 |

TABLE 8

| TGSNN + Q192S + L193X | |
|---|---|
| TGSNN + Q192S | 12 |
| TGSNN + Q192G + L193E | 4.2 |
| TGSNN + Q192S + L193G | 6.8 |
| TGSNN + Q192S + L193A | 7.3 |
| TGSNN + Q192S + L193K | 3.7 |
| TGSNN + Q192S + L193R | 7.7 |
| TGSNN + Q192S + L193H | 8.3 |
| TGSNN + Q192S + L193D | 6.8 |
| TGSNN + Q192S + L193E | 4.3 |
| TGSNN + Q192S + L193N | 8.9 |
| TGSNN + Q192S + L193Q | 11 |
| TGSNN + Q192S + L193S | 5.7 |
| TGSNN + Q192S + L193T | 6.3 |
| TGSNN + Q192S + L193Y | 7.4 |
| TGSNN + Q192S + L193C | 9.3 |
| TGSNN + Q192S + L193M | 4.0 |
| TGSNN + Q192S + L193F | 7.8 |
| TGSNN + Q192S + L193W | 8.2 |
| TGSNN + Q192S + L193V | 7.0 |
| TGSNN + Q192S + L193I | 6.9 |
| TGSNN + Q192S + L193P | 6.1 |

TABLE 9

| | |
|---|---|
| Wild Type | 79 |
| TGSNN | 42 |
| TGSNN + Q192S | 12 |
| TGSNN + N452P | 14 |
| TGSNN + Q192G + L193E | 4.2 |
| TGSNN + Q192S + L193M | 4.0 |
| TGSNN + Q192S + L193T | 5.8 |
| TGSNN + Q192S + N452P | 1.9 |
| TGSNN + Q192G + N452P | 1.6 |
| TGSNN + Y367A + N452P | 50 |
| TGSNN + Y367F + N452P | 12 |
| TGSNN + Y367W + N452P | 15 |
| TGSNN + Q192S + Y367A + N452P | nd |
| TGSNN + Q192S + Y367F + N452P | 2.7 |
| TGSNN + Q192S + Y367W + N452P | 2.0 |
| TGSNN + L193E + N452P | 1.0 |
| TGSNN + Q192G + L193E + N452P | 0.6 |

TABLE 10

| | |
|---|---|
| Wild Type | 79 |
| G451C | 74 |
| TCSRN | 33 |
| TCSRN + G451C | 44 |
| N452P | 30 |
| TGSNN + Q192S + L193M | 4.0 |
| TGSNN + Q192S + L193M + N452P | 0.8 |
| TGSNN + Q192G + L193E + E277K | 2.7 |
| TGSNN + Q192G + L193E + N452P | 0.6 |
| TGSNN + N452P | 14 |
| TGSNN + A318Y + N452P | 7.8 |

TABLE 11

| TGSXN + Q192S + N452P | |
|---|---|
| TGSAN + Q192S + N452P | 7.6 |
| TGSCN + Q192S + N452P | 3.9 |
| TGSDN + Q192S + N452P | 3.6 |
| TGSFN + Q192S + N452P | 26 |
| TGSGN + Q192S + N452P | 3.6 |
| TGSLN + Q192S + N452P | 2.2 |
| TGSMN + Q192S + N452P | 2.5 |
| TGSNN + Q192S + N452P | 1.9 |
| TGSPN + Q192S + N452P | 19 |
| TGSSN + Q192S + N452P | 7.4 |
| TGSTN + Q192S + N452P | 3.8 |
| TGSVN + Q192S + N452P | 3.7 |
| TGSIN + Q192S + N452P | 3.4 |
| TGSWN + Q192S + N452P | 1.2 |
| TGSYN + Q192S + N452P | 1.4 |
| TGSEN + Q192S + N452P | 5.8 |
| TGSHN + Q192S + N452P | 4.0 |
| TGSQN + Q192S + N452P | 5.1 |
| TGSRN + Q192S + N452P | 1.5 |

TABLE 12

| TGSXN + Q192G + L193E + N452P | |
|---|---|
| TGSAN + Q192G + L193E + N452P | 4.1 |
| TGSFN + Q192G + L193E + N452P | nd |
| TGSHN + Q192G + L193E + N452P | 2.3 |
| TGSIN + Q192G + L193E + N452P | 1.6 |
| TGSLN + Q192G + L193E + N452P | 1.4 |
| TGSNN + Q192G + L193E + N452P | 0.6 |
| TGSQN + Q192G + L193E + N452P | 8.4 |
| TGSTN + Q192G + L193E + N452P | nd |
| TGSVN + Q192G + L193E + N452P | 2.3 |
| TGSCN + Q192G + L193E + N452P | 44 |
| TGSDN + Q192G + L193E + N452P | 7.2 |
| TGSMN + Q192G + L193E + N452P | 7.3 |
| TGSKN + Q192G + L193E + N452P | 2.4 |
| TGSPN + Q192G + L193E + N452P | 5.4 |
| TGSRN + Q192G + L193E + N452P | 3.1 |
| TGSSN + Q192G + L193E + N452P | 5.2 |
| TGSWN + Q192G + L193E + N452P | 2.7 |
| TGSYN + Q192G + L193E + N452P | 3.1 |

TABLE 13

| TGSXN + Q192S + N452P | |
|---|---|
| TGSNN | 42 |
| TGSKN | 43 |
| TGSRN | 43 |
| TGSWN | 33 |
| TGSNN + Q192S | 12 |
| TGSKN + Q192S | 14 |
| TGSRN + Q192S | 8.1 |
| TGSWN + Q192S | 7.2 |
| TGSNN + N452P | 14 |
| TGSKN + N452P | 16 |
| TGSRN + N452P | 15 |
| TGSWN + N452P | 10 |
| TGSNN + Q192S + N452P | 1.9 |
| TGSKN + Q192S + N452P | 1.8 |
| TGSRN + Q192S + N452P | 1.5 |
| TGSWN + Q192S + N452P | 1.2 |

TABLE 14

| TGSNN + Q192S + L193X + A318Y + N452P | |
|---|---|
| TGSNN + Q192S + L193M + N452P | 0.8 |
| TGSNN + Q192S + A318Y + N452P | 1.5 |
| TGSNN + Q192S + L193G + A318Y + N452P | 1.0 |
| TGSNN + Q192S + L193A + A318Y + N452P | 8.8 |
| TGSNN + Q192S + L193K + A318Y + N452P | 0.5 |
| TGSNN + Q192S + L193R + A318Y + N452P | 8.8 |
| TGSNN + Q192S + L193H + A318Y + N452P | 9.0 |
| TGSNN + Q192S + L193D + A318Y + N452P | 7.8 |
| TGSNN + Q192S + L193E + A318Y + N452P | 6.6 |
| TGSNN + Q192S + L193N + A318Y + N452P | 1.4 |
| TGSNN + Q192S + L193Q + A318Y + N452P | 2.2 |
| TGSNN + Q192S + L193S + A318Y + N452P | 1.0 |
| TGSNN + Q192S + L193T + A318Y + N452P | 8.5 |
| TGSNN + Q192S + L193Y + A318Y + N452P | 8.1 |
| TGSNN + Q192S + L193C + A318Y + N452P | 8.9 |
| TGSNN + Q192S + L193M + A318Y + N452P | 2.4 |
| TGSNN + Q192S + L193F + A318Y + N452P | 8.4 |
| TGSNN + Q192S + L193W + A318Y + N452P | 9.0 |
| TGSNN + Q192S + L193V + A318Y + N452P | 0.9 |
| TGSNN + Q192S + L193I + A318Y + N452P | 7.7 |
| TGSNN + Q192S + L193P + A318Y + N452P | 8.2 |

TABLE 15

| TGSNN + Q192S + A318X + N452P | |
|---|---|
| TGSNN + Q192S + N452P | 1.9 |
| TGSNN + Q192S + A318G + N452P | 2.6 |
| TGSNN + Q192S + A318K + N452P | 0.0 |
| TGSNN + Q192S + A318R + N452P | 3.0 |
| TGSNN + Q192S + A318H + N452P | 2.0 |
| TGSNN + Q192S + A318D + N452P | 2.1 |
| TGSNN + Q192S + A318E + N452P | 2.3 |
| TGSNN + Q192S + A318N + N452P | 2.4 |
| TGSNN + Q192S + A318Q + N452P | 2.8 |
| TGSNN + Q192S + A318S + N452P | nd |
| TGSNN + Q192S + A318T + N452P | 5.1 |
| TGSNN + Q192S + A318Y + N452P | 2.3 |
| TGSNN + Q192S + A318C + N452P | nd |
| TGSNN + Q192S + A318M + N452P | 3.0 |
| TGSNN + Q192S + A318F + N452P | 3.0 |
| TGSNN + Q192S + A318W + N452P | 0.1 |
| TGSNN + Q192S + A318V + N452P | 0.4 |
| TGSNN + Q192S + A318L + N452P | 3.0 |
| TGSNN + Q192S + A318I + N452P | 4.5 |
| TGSNN + Q192S + A318P + N452P | nd |

TABLE 16

| TGSNN + Q192G + L193E + A318X + N452P | |
|---|---|
| TGSNN + Q192G + L193E + N452P | 0.6 |
| TGSNN + Q192G + L193E + A318G + N452P | 0.7 |
| TGSNN + Q192G + L193E + A318K + N452P | 0.7 |
| TGSNN + Q192G + L193E + A318R + N452P | 0.7 |
| TGSNN + Q192G + L193E + A318H + N452P | 0.8 |
| TGSNN + Q192G + L193E + A318D + N452P | 1.0 |
| TGSNN + Q192G + L193E + A318E + N452P | 0.9 |
| TGSNN + Q192G + L193E + A318N + N452P | 0.6 |
| TGSNN + Q192G + L193E + A318Q + N452P | 0.5 |
| TGSNN + Q192G + L193E + A318S + N452P | 0.6 |
| TGSNN + Q192G + L193E + A318T + N452P | nd |
| TGSNN + Q192G + L193E + A318Y + N452P | 1.0 |
| TGSNN + Q192G + L193E + A318C + N452P | 0.7 |
| TGSNN + Q192G + L193E + A318M + N452P | 0.5 |
| TGSNN + Q192G + L193E + A318F + N452P | 0.8 |
| TGSNN + Q192G + L193E + A318W + N452P | 1.0 |
| TGSNN + Q192G + L193E + A318V + N452P | nd |
| TGSNN + Q192G + L193E + A318L + N452P | 0.6 |
| TGSNN + Q192G + L193E + A318I + N452P | 1.9 |
| TGSNN + Q192G + L193E + A318P + N452P | nd |

TABLE 17

| TGSI(K, R, W)N | |
|---|---|
| TGSNN | 42 |
| TGSKN | 43 |
| TGSRN | 43 |
| TGSWN | 33 |
| TGSNN + Q192S | 12 |
| TGSKN + Q192S | 14 |
| TGSRN + Q192S | 8.1 |
| TGSWN + Q192S | 7.2 |
| TGSNN + N452P | 14 |
| TGSKN + N452P | 16 |
| TGSRN + N452P | 15 |
| TGSWN + N452P | 10 |
| TGSNN + Q192S + N452P | 1.9 |
| TGSKN + Q192S + N452P | 1.8 |
| TGSRN + Q192S + N452P | 1.5 |
| TGSWN + Q192S + N452P | 1.2 |

TABLE 18

| TGSN | |
|---|---|
| TGSN | nd |
| TGSN + N452P | 38 |
| TGSN + Q192S + N452P | 9.5 |
| TGSN + Q192G + L193E | 11 |
| TGSN + Q192G + L193E + N452P | 2.5 |
| TGSN + Q192S + L193M | 16 |
| TGSN + Q192S + L193M + N452P | 5.5 |

TABLE 19

| TGNN | |
|---|---|
| TGNN | 38 |
| TGNN + N452P | 22 |
| TGNN + Q192S + N452P | 5.3 |
| TGNN + Q192G + L193E | 11 |
| TGNN + Q192G + L193E + N452P | 2.1 |
| TGNN + Q192S + L193M | 17 |
| TGNN + Q192S + L193M + N452P | 2.3 |

As is clear from, the tables, the modified. PQQGDH of the present invention in all cases exhibited a reactivity for glucose that was higher than that for maltose.

EXAMPLE 4

Fabrication and Evaluation of an Enzyme Sensor 20 mg carbon paste was added, to 5 units of the modified PQQGDH of the present invention and freeze-dried. After thorough mixing, it was filled onto the surface of a carbon paste electrode that carries approximately 40 mg carbon paste, and polished on filter paper. The electrode was treated for 30 minutes at room temperature in 10 mM MOPS buffer (pH 7.0) containing 1% glutaraldehyde, and then treated for 20 minutes at room temperature in 10 mM MOPS buffer (pH 7.0) containing 20 mM lysine in order to block the glutaraldehyde. The electrode was equilibrated for at least one hour at room temperature in 10 mM MOPS buffer (pH 7.0). The electrode was stored at 4° C.

The glucose concentration was measured using the enzyme sensor prepared above. Glucose was quantitatively measured in the range from 0.1 mM to 5 mM using the enzyme sensor having immobilised the modified PQQGDH of the present invention.

EXAMPLE 5

Measurement of the Enzymatic Activity Using a Purified Enzyme Preparation

A cation-exchange chromatography column packed with TSEgel CM-TOYOPEARL 650M (Tosoh Corporation) was equilibrated with 10 mM phosphate buffer at pH 7.0 and the wild-type crude enzyme or the modified PQQGDH crude enzymes obtained in Example 2 was adsorbed on the column. The column was washed with 750 mL 10 mM phosphate buffer (pH 7.0) and the enzyme was then eluted with 10 mM phosphate buffer (pH 7.0) containing from 0 to 0.2 M NaCl. The flow rate was 5 mL/minute. The fraction exhibiting GDH activity was collected and was dialyzed overnight against 10 mM MOPS-NaOH buffer (pH 7.0) to obtain an electrophoretically-homogeneous modified PQQGDH protein. The enzymatic activity of the purified enzyme preparations for glucose and maltose was measured as in Example 4. Typical results are shown in the following table.

TABLE 20

| MODIFIED PQQGDH | ENZYMATIC ACTIVITY (Glu; 4 mM) (U/mg) | Mal:Glu (%) 4:4 | Mal:Glu (%) 40:4 |
|---|---|---|---|
| TGSNN + Q192G + L193E | 357 | 4.1 | 28* |
| TGSNN + Q192S + N452P | 723 | 3.5 | 19* |
| TGSNN + Q192G + L193E + N452P | 213 | 0.56 | 5.7 |
| TGSNN + Q192S + L193M + N452P | 285 | 2.0 | 16* |
| TGSNN + Q192G + L193E + A318K + N452P | 381 | 0.99 | 8.92 |
| TGSNN + Q192G + L193E + A318Q + N452P | 469 | 0.55 | 6.74 |

*measured at Mal:Glu = 50:5

In addition, the enzymatic activity for glucose and maltose of the modified PQQGDH having the TGSNN+Q192G+L193E+N452P mutations is shown in FIG. 1.

EXAMPLE 6

Comparison with Prior-Art Modified PQQGDHs

The enzymatic activity for glucose and maltose was measured as in Example 4 using the wild-type crude enzyme obtained in Example 2, the modified PQQGDH crude enzymes obtained in Example 2, and, for comparison, prior-art modified PQQGDHs lacking the mutation at amino acid residue G at Position 99 of PQQGDH but having the 1 or 2 or more amino acid substitutions at other positions.

The following table shows typical results for the enzymatic activity of the modified PQQGDH of the present invention having various mutations and substitution of 99G with TGSNN, a comparative PQQGDH having the same mutation(s) but not substitution at 99G and wild-type PQQGDH. The results are expressed by the activity for 4 mM glucose or 10 mM glucose and for the ratio of the activity for maltose to the activity for glucose (%, 4 mM maltose:4 mM glucose or 10 mM:10 mM).

TABLE 21

| | ACTIVITY FOR GLUCOSE (U/mg) | | Mal/Glu (%) | |
|---|---|---|---|---|
| | 4 mM | 10 mM | 4:4 | 10:10 |
| WILD TYPE | 47.69 | 86.96 | 73.5 | 75.5 |
| TGSNN + Q192G + L193E | 10.63 | 20.20 | 4.2 | 5.1 |
| Q192G + L193E | 6.11 | 11.62 | 9.0 | 10.5 |
| TGSNN + Q192G | 15.90 | 26.36 | 9.1 | 11.9 |
| Q192G | 19.30 | 31.79 | 20.2 | 26.1 |
| TGSNN + Q192A | 26.26 | 48.56 | 7.8 | 9.9 |
| Q192A | 21.44 | 41.32 | 15.2 | 18.2 |
| TGSNN + Q192S | 35.83 | 60.94 | 12.9 | 17.0 |
| Q192S | 26.66 | 44.91 | 28.0 | 37.8 |
| TGSNN + N452P | 58.71 | 110.01 | 16.3 | 18.7 |
| N452P | 56.53 | 103.43 | 26.4 | 33.1 |

TABLE 21-continued

| | ACTIVITY FOR GLUCOSE (U/mg) | | Mal/Glu (%) | |
|---|---|---|---|---|
| | 4 mM | 10 mM | 4:4 | 10:10 |
| TGSNN + Q192S + N452P | 37.98 | 72.23 | 1.5 | 2.2 |
| Q192S + N452P | 28.93 | 56.12 | 5.0 | 6.6 |

As shown in the table, the enzymatic activity of the modified enzymes according to the present invention with the insertion of the TGSNN sequence for glucose is either maintained or increased compared to the corresponding modified enzymes having the same mutations but lacking the insertion of TGSNN. In addition, the maltose-versus-glucose activity ratio is reduced to about one-half to one-fifth, and the selectivity for glucose is thus improved. For example, it has already been reported that the substrate specificity is increased in the modified PQQGDH having a double mutation Q192G/L193E. The activity of the Q192G/L193E modified PQQGDH for a mM glucose was 6.1 U/mg and the 4 mM maltose-versus-4 mM glucose activity ratio was 9%. In contrast, the additional insertion of TGSNN provided an approximately 1.7-fold increase in the activity for 4 mM glucose to 10.63 U/mg, and a 2.14-fold increase in substrate specificity, with 4.2% for the 4 mM maltose-versus-4 mM glucose activity ratio.

As demonstrated by these results, the modified PQQGDH of the present invention has a high enzymatic activity for glucose and a high substrate specificity for glucose over maltose.

INDUSTRIAL APPLICABILITY

The present invention is useful for assaying glucose and particularly for measuring blood sugar level.

The invention claimed is:

1. A modified pyrroloquinoline quinone glucose dehydrogenase, wherein the amino acid residue G at Position 100 of a pyrroloquinoline quinone glucose dehydrogenase (PQQGDH) of SEQ ID NO: 3 is substituted by the amino acid sequence TGZN (where Z is SX, S, or N and X is any amino acid residue), and from 1 to 10 of amino acid residues at Positions 1 to 99 or at Positions 101 to 480 of SEQ ID NO: 3 are optionally substituted by any other amino acid residue(s).

2. The modified pyrroloquinoline quinone glucose dehydrogenase according to claim 1, wherein Z is SX where X is any amino acid residue.

3. The modified pyrroloquinoline quinone glucose dehydrogenase according to claim 1, wherein Z is SN.

4. The modified pyrroloquinoline quinone glucose dehydrogenase according to claim 1, further comprising one or more substitutions selected from the group consisting of the following amino acid substitutions:

Q193G, Q193A, or Q193S;

L194X where X is any amino acid residue;
E278X where X is any amino acid residue;
A320X where X is any amino acid residue;
Y369A, Y369F, or Y369W;
G453C; and
N454X,
where X is any amino acid residue.

5. The modified pyrroloquinoline quinone glucose dehydrogenase according to claim 4, comprising any of the following combinations of amino acid substitutions:

G100(TGSXN)+Q193G+L194E;
G100(TGSXN)+Q193S+N454P;
G100(TGSXN)+Q193G+L194E+N454P;
G100(TGSXN)+Q193S+N454P;
G100(TGSNN)+N454P;
G100(TGSNN)+Q193G+L194E+N454P;
G100(TGSNN)+Q193S+N454P;
G100(TGSNN)+Q193G+N454P;
G100(TGSNN)+L194E+N454P;
G100(TGSNN)+Q193S+L194M+N454P;
G100(TGSNN)+A320Y+N454P;
G100(TGSNN)+Q193G;
G100(TGSNN)+Q193S;
G100(TGSNN)+Q193A;
G100(TGSNN)+Q193G+L194E;
G100(TGSNN)+Q193S+L194X;
G100(TGSNN)+Q193S+L194M;
G100(TGSNN)+Q193S+L194T;
G100(TGSNN)+Q193S+E278X;
G100(TGSNN)+Q193S+N454X;
G100(TGSNN)+Q193S+L194X+A320Y+N454P;
G100(TGSNN)+Q193S+A320X+N454P;
G100(TGSNN)+Q193G+L194E+A320X+N454P;
G100(TGSKN)+Q193S+N454P;
G100(TGSRN)+Q193S+N454P;
G100(TGSWN)+Q193S+N454P;
G100(TGSN)+Q193S+N454P;
G100(TGSN)+Q193G+L194E;
G100(TGSN)+Q193S+L194M;
G100(TGNN)+Q193S+N454P;
G100(TGNN)+Q193G+L194E; or
G100(TGNN)+Q193S+L194M,
where X is any amino acid residue.

6. The modified pyrroloquinoline quinone glucose dehydrogenase according to claim 5, comprising any of the following combinations of amino acid substitutions:

G100(TGSXN)+Q193G+L194E;
G100(TGSXN)+Q193S+N454P;
G100(TGSNN)+Q193G+L194E+N454P;
G100(TGSNN)+Q193S+L194M+N454P;
G100(TGSNN)+Q193G+L194E+A320K+N454P; or
G100(TGSNN)+Q193G+L194E+A320Q+N454P.

7. A glucose assay kit comprising the modified pyrroloquinoline quinone glucose dehydrogenase according to claim 1.

8. An enzyme electrode comprising the modified pyrroloquinoline quinone glucose dehydrogenase according to claim 1.

9. A glucose sensor comprising the enzyme electrode according to claim 8 as a working electrode.

10. The modified pyrroloquinoline quinone glucose dehydrogenase according to claim 1, wherein from 1 to 10 of amino acid residues at Positions 1 to 99 or at Positions 101 to 480 of SEQ ID NO: 3 are substituted by any other amino acid residue(s).

11. The modified pyrroloquinoline quinone glucose dehydrogenase according to claim 1, wherein the amino acid residues at Positions 1 to 99 and at Positions 101 to 480 of SEQ ID NO: 3 are not substituted by any other amino acid residue(s).

12. A method for analyzing glucose level using the modified pyrroloquinoline quinone glucose dehydrogenase according to claim 1.

* * * * *

SEQUENCE LISTING

```
<160> NUMBER OF SEQ ID NOS: 60

<210> SEQ ID NO 1
<211> LENGTH: 478
<212> TYPE: PRT
<213> ORGANISM: Acinetobacter calcoaceticus

<400> SEQUENCE: 1

Met Asn Lys His Leu Leu Ala Lys Ile Ala Leu Leu Ser Ala Val Gln
1               5                   10                  15

Leu Val Thr Leu Ser Ala Phe Ala Asp Val Pro Leu Thr Pro Ser Gln
                20                  25                  30

Phe Ala Lys Ala Lys Ser Glu Asn Phe Asp Lys Lys Val Ile Leu Ser
            35                  40                  45

Asn Leu Asn Lys Pro His Ala Leu Leu Trp Gly Pro Asp Asn Gln Ile
        50                  55                  60

Trp Leu Thr Glu Arg Ala Thr Gly Lys Ile Leu Arg Val Asn Pro Glu
65                  70                  75                  80

Ser Gly Ser Val Lys Thr Val Phe Gln Val Pro Glu Ile Val Asn Asp
                85                  90                  95

Ala Asp Gly Gln Asn Gly Leu Leu Gly Phe Ala Phe His Pro Asp Phe
            100                 105                 110

Lys Asn Asn Pro Tyr Ile Tyr Ile Ser Gly Thr Phe Lys Asn Pro Lys
        115                 120                 125

Ser Thr Asp Lys Glu Leu Pro Asn Gln Thr Ile Ile Arg Arg Tyr Thr
    130                 135                 140

Tyr Asn Lys Ser Thr Asp Thr Leu Glu Lys Pro Val Asp Leu Leu Ala
145                 150                 155                 160

Gly Leu Pro Ser Ser Lys Asp His Gln Ser Gly Arg Leu Val Ile Gly
                165                 170                 175

Pro Asp Gln Lys Ile Tyr Tyr Thr Ile Gly Asp Gln Gly Arg Asn Gln
            180                 185                 190

Leu Ala Tyr Leu Phe Leu Pro Asn Gln Ala Gln His Thr Pro Thr Gln
        195                 200                 205

Gln Glu Leu Asn Gly Lys Asp Tyr His Thr Tyr Met Gly Lys Val Leu
    210                 215                 220

Arg Leu Asn Leu Asp Gly Ser Ile Pro Lys Asp Asn Pro Ser Phe Asn
225                 230                 235                 240

Gly Val Val Ser His Ile Tyr Thr Leu Gly His Arg Asn Pro Gln Gly
```

```
                    245                 250                 255
Leu Ala Phe Thr Pro Asn Gly Lys Leu Leu Gln Ser Glu Gln Gly Pro
                260                 265                 270

Asn Ser Asp Asp Glu Ile Asn Leu Ile Val Lys Gly Gly Asn Tyr Gly
            275                 280                 285

Trp Pro Asn Val Ala Gly Tyr Lys Asp Asp Ser Gly Tyr Ala Tyr Ala
        290                 295                 300

Asn Tyr Ser Ala Ala Asn Lys Ser Ile Lys Asp Leu Ala Gln Asn
305                 310                 315                 320

Gly Val Lys Val Ala Gly Val Pro Val Thr Lys Glu Ser Glu Trp
                325                 330                 335

Thr Gly Lys Asn Phe Val Pro Pro Leu Lys Thr Leu Tyr Thr Val Gln
                340                 345                 350

Asp Thr Tyr Asn Tyr Asn Asp Pro Thr Cys Gly Glu Met Thr Tyr Ile
            355                 360                 365

Cys Trp Pro Thr Val Ala Pro Ser Ser Ala Tyr Val Tyr Lys Gly Gly
        370                 375                 380

Lys Lys Ala Ile Thr Gly Trp Glu Asn Thr Leu Leu Val Pro Ser Leu
385                 390                 395                 400

Lys Arg Gly Val Ile Phe Arg Ile Lys Leu Asp Pro Thr Tyr Ser Thr
                405                 410                 415

Thr Tyr Asp Asp Ala Val Pro Met Phe Lys Ser Asn Asn Arg Tyr Arg
            420                 425                 430

Asp Val Ile Ala Ser Pro Asp Gly Asn Val Leu Tyr Val Leu Thr Asp
        435                 440                 445

Thr Ala Gly Asn Val Gln Lys Asp Asp Gly Ser Val Thr Asn Thr Leu
    450                 455                 460

Glu Asn Pro Gly Ser Leu Ile Lys Phe Thr Tyr Lys Ala Lys
465                 470                 475

<210> SEQ ID NO 2
<211> LENGTH: 1612
<212> TYPE: DNA
<213> ORGANISM: Acinetobacter calcoaceticus

<400> SEQUENCE: 2
agctactttt atgcaacaga gcctttcaga aatttagatt ttaatagatt cgttattcat    60
cataatacaa atcatataga gaactcgtac aaacccttta ttagaggttt aaaaattctc   120
ggaaaatttt gacaatttat aaggtggaca catgaataaa catttattgg ctaaaattgc   180
tttattaagc gctgttcagc tagttacact ctcagcattt gctgatgttc ctctaactcc   240
atctcaattt gctaaagcga atcagagaa ctttgacaag aaagttattc tatctaatct   300
aaataagccg catgctttgt tatggggacc agataatcaa atttggttaa ctgagcgagc   360
aacaggtaag attctaagag ttaatccaga gtcgggtagt gtaaaaacag tttttcaggt   420
accagagatt gtcaatgatg ctgatgggca gaatggttta ttaggttttg ccttccatcc   480
tgattttaaa aataatcctt atatctatat ttcaggtaca tttaaaaatc gaaatctac    540 agataaagaa ttaccgaacc aaacgattat tcgtcgttat acctataata atcaacaga   600 tacgctcgag aagccagtcg atttattagc aggattacct tcatcaaaag accatcagtc   660
aggtcgtctt gtcattgggc cagatcaaaa gatttattat acgattggtg accaagggcg   720
taaccagctt gcttatttgt tcttgccaaa tcaagcacaa catacgccaa ctcaacaaga   780
actgaatggt aaagactatc acacctatat gggtaaagta ctacgcttaa atcttgatgg   840
```

```
aagtattcca aaggataatc caagttttaa cggggtggtt agccatattt atacacttgg    900
acatcgtaat ccgcagggct tagcattcac tccaaatggt aaattattgc agtctgaaca    960
aggcccaaac tctgacgatg aaattaacct cattgtcaaa ggtggcaatt atggttggcc   1020
gaatgtagca ggttataaag atgatagtgg ctatgcttat gcaaattatt cagcagcagc   1080
caataagtca attaaggatt tagctcaaaa tggagtaaaa gtagccgcag gggtccctgt   1140
gacgaaagaa tctgaatgga ctggtaaaaa ctttgtccca ccattaaaaa ctttatatac   1200
cgttcaagat acctacaact ataacgatcc aacttgtgga gagatgacct acatttgctg   1260
gccaacagtt gcaccgtcat ctgcctatgt ctataagggc ggtaaaaaag caattactgg   1320
ttgggaaaat acattattgg ttccatcttt aaaacgtggt gtcattttcc gtattaagtt   1380
agatccaact tatagcacta cttatgatga cgctgtaccg atgtttaaga gcaacaaccg   1440
ttatcgtgat gtgattgcaa gtccagatgg gaatgtctta tatgtattaa ctgatactgc   1500
cggaaatgtc caaaagatg atggctcagt aacaaataca ttagaaaacc caggatctct   1560
cattaagttc acctataagg ctaagtaata cagtcgcatt aaaaaaccga tc           1612
```

<210> SEQ ID NO 3
<211> LENGTH: 480
<212> TYPE: PRT
<213> ORGANISM: Acinetobacter baumannii

<400> SEQUENCE: 3

```
Met Asn Lys His Leu Leu Ala Lys Ile Thr Leu Leu Gly Ala Ala Gln
1               5                   10                  15

Leu Phe Thr Phe His Thr Ala Phe Ala Asp Ile Pro Leu Thr Pro Ala
            20                  25                  30

Gln Phe Ala Lys Ala Lys Thr Glu Asn Phe Asp Lys Lys Val Ile Leu
        35                  40                  45

Ser Asn Leu Asn Lys Pro His Ala Leu Leu Trp Gly Pro Asp Asn Gln
    50                  55                  60

Ile Trp Leu Thr Glu Arg Ala Thr Gly Lys Ile Leu Arg Val Asn Pro
65                  70                  75                  80

Val Ser Gly Ser Ala Lys Thr Val Phe Gln Val Pro Glu Ile Val Ser
                85                  90                  95

Asp Ala Asp Gly Gln Asn Gly Leu Leu Gly Phe Ala Phe His Pro Asp
            100                 105                 110

Phe Lys His Asn Pro Tyr Ile Tyr Ile Ser Gly Thr Phe Lys Asn Pro
        115                 120                 125

Lys Ser Thr Asp Lys Glu Leu Pro Asn Gln Thr Ile Ile Arg Arg Tyr
    130                 135                 140

Thr Tyr Asn Lys Thr Thr Asp Thr Phe Glu Lys Pro Ile Asp Leu Ile
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Ser Asn Gln Ala Gln His Thr Pro Thr
        195                 200                 205

Gln Gln Glu Leu Asn Ser Lys Asp Tyr His Thr Tyr Met Gly Lys Val
    210                 215                 220

Leu Arg Leu Asn Leu Asp Gly Ser Ile Pro Lys Asp Asn Pro Ser Phe
225                 230                 235                 240
```

-continued

Asn Gly Val Val Ser His Ile Tyr Thr Leu Gly His Arg Asn Pro Gln
            245                 250                 255

Gly Leu Ala Phe Ala Pro Asn Gly Lys Leu Leu Gln Ser Glu Gln Gly
        260                 265                 270

Pro Asn Ser Asp Asp Glu Ile Asn Leu Val Leu Lys Gly Gly Asn Tyr
    275                 280                 285

Gly Trp Pro Asn Val Ala Gly Tyr Lys Asp Asp Ser Gly Tyr Ala Tyr
        290                 295                 300

Ala Asn Tyr Ser Ala Ala Thr Asn Lys Ser Gln Ile Lys Asp Leu Ala
305                 310                 315                 320

Gln Asn Gly Ile Lys Val Ala Thr Gly Val Pro Val Thr Lys Glu Ser
                325                 330                 335

Glu Trp Thr Gly Lys Asn Phe Val Pro Pro Leu Lys Thr Leu Tyr Thr
            340                 345                 350

Val Gln Asp Thr Tyr Asn Tyr Asn Asp Pro Thr Cys Gly Glu Met Ala
        355                 360                 365

Tyr Ile Cys Trp Pro Thr Val Ala Pro Ser Ser Ala Tyr Val Tyr Thr
    370                 375                 380

Gly Gly Lys Lys Ala Ile Pro Gly Trp Glu Asn Thr Leu Leu Val Pro
385                 390                 395                 400

Ser Leu Lys Arg Gly Val Ile Phe Arg Ile Lys Leu Asp Pro Thr Tyr
                405                 410                 415

Ser Thr Thr Leu Asp Asp Ala Ile Pro Met Phe Lys Ser Asn Asn Arg
            420                 425                 430

Tyr Arg Asp Val Ile Ala Ser Pro Glu Gly Asn Thr Leu Tyr Val Leu
        435                 440                 445

Thr Asp Thr Ala Gly Asn Val Gln Lys Asp Asp Gly Ser Val Thr His
    450                 455                 460

Thr Leu Glu Asn Pro Gly Ser Leu Ile Lys Phe Thr Tyr Asn Gly Lys
465                 470                 475                 480

<210> SEQ ID NO 4
<211> LENGTH: 1443
<212> TYPE: DNA
<213> ORGANISM: Acinetobacter baumannii

<400> SEQUENCE: 4
atgaataaac aatttattagc aaaaatcact cttttaggtg ctgcacaact atttacgttt      60
catacggcat ttgcagatat acctctgaca cctgctcagt tcgcaaaagc gaaaacagaa     120
aattttgata aaaagtgat tctgtccaat ttaaataaac cacatgcttt gttatggggg     180
ccagataatc aaatttggtt aaccgaacgt gcaactggca aaattttaag agtaaatcct     240
gtatctggta gcgcgaaaac agtatttcag gttcctgaaa ttgtgagtga tgctgatggg     300
caaaatggtt tgttaggttt tgcttttcat cctgacttta acataaccc ttatatctat     360 atttcaggca cttttaaaaa tccaaaatct acagataaag agttacctaa tcagacaatt     420
attcgtagat ataccctataa taaaactaca gatacatttg aaaagcctat tgatttgatt     480
gcaggtttac cgtcatcaaa agatcatcag tctggtcgtc tcgttattgg tccagaccaa     540
aaaatctact atacgattgg tgaccaaggt cgtaatcagt tagcttatct attcttatcg     600
aatcaggcac agcatactcc gactcagcaa gagctcaata gtaaagacta ccatacatat     660
atgggtaaag tattacgctt aaatctggac ggcagtatac ctaaagacaa cccaagcttt     720
aacggcgtag tgagtcatat ctacactta gggcaccgta atccacaagg tttagcattt     780

-continued

```
gccccaaatg gaaagctttt acaatctgag caagggccaa attctgatga tgaaattaac    840
cttgtattaa aaggtggtaa ctatggctgg ccaaatgtag ctggttataa agatgacagt    900
ggttatgcct atgcaaacta ttcggcagca accaataaat cacaaattaa agatttagct    960
caaaacggga taaagtagc aacaggtgtt cctgtgacta aagagtctga atggactggt    1020
aaaaactttg tgccacccttt gaaaacttta tatacggtac aagataccta taactataat   1080
gaccctactt gtggtgagat ggcatatatt tgctggccaa cggttgcacc gtcatcggca    1140
tatgtatata cgggaggcaa aaaagcgatt ccagggtggg aaaatacatt attggtccca    1200
tctttaaaac gtgggtgat tttccgtatt aaattggacc cgacatatag cacgactttg    1260
gatgatgcta tcccaatgtt taaaagcaat aaccgttatc gtgatgtcat cgctagtcca    1320
gaaggtaata ccttatatgt gctgactgat acagcgggaa atgtacaaaa agatgatggt    1380
tcagtcactc atactttaga gaatcccggt tctctcatta aatttacata taacggtaag    1440
taa                                                                  1443
```

<210> SEQ ID NO 5
<211> LENGTH: 28
<212> TYPE: DNA
<213> ORGANISM: Artificial Sequence
<220> FEATURE:
<223> OTHER INFORMATION: PCR primer

<400> SEQUENCE: 5
aacagaccat ggataaacat ttattggc                                       28

<210> SEQ ID NO 6
<211> LENGTH: 29
<212> TYPE: DNA
<213> ORGANISM: Artificial Sequence
<220> FEATURE:
<223> OTHER INFORMATION: PCR primer

<400> SEQUENCE: 6
acagccaagc ttttacttag ccttatagg                                      29

<210> SEQ ID NO 7
<211> LENGTH: 33
<212> TYPE: DNA
<213> ORGANISM: Artificial Sequence
<220> FEATURE:
<223> OTHER INFORMATION: PCR primer

<400> SEQUENCE: 7
actggaaata atcagaatgg tttattaggt ttt                                 33

<210> SEQ ID NO 8
<211> LENGTH: 33
<212> TYPE: DNA
<213> ORGANISM: Artificial Sequence
<220> FEATURE:
<223> OTHER INFORMATION: PCR primer

<400> SEQUENCE: 8
ctgattattt ccagtatcag catcattgac aat                                 33

<210> SEQ ID NO 9
<211> LENGTH: 33
<212> TYPE: DNA
<213> ORGANISM: Artificial Sequence
<220> FEATURE:

<223> OTHER INFORMATION: PCR primer

<400> SEQUENCE: 9
actggacaga atcagaatgg tttattaggt ttt                           33

<210> SEQ ID NO 10
<211> LENGTH: 33
<212> TYPE: DNA
<213> ORGANISM: Artificial Sequence
<220> FEATURE:
<223> OTHER INFORMATION: PCR primer

<400> SEQUENCE: 10
ctgattctgt ccagtatcag catcattgac aat                           33

<210> SEQ ID NO 11
<211> LENGTH: 33
<212> TYPE: DNA
<213> ORGANISM: Artificial Sequence
<220> FEATURE:
<223> OTHER INFORMATION: PCR primer

<400> SEQUENCE: 11
actggaagca atcagaatgg tttattaggt ttt                           33

<210> SEQ ID NO 12
<211> LENGTH: 33
<212> TYPE: DNA
<213> ORGANISM: Artificial Sequence
<220> FEATURE:
<223> OTHER INFORMATION: PCR primer

<400> SEQUENCE: 12
ctgattgctt ccagtatcag catcattgac aat                           33

<210> SEQ ID NO 13
<211> LENGTH: 33
<212> TYPE: DNA
<213> ORGANISM: Artificial Sequence
<220> FEATURE:
<223> OTHER INFORMATION: PCR primer

<400> SEQUENCE: 13
actggaggta atcagaatgg tttattaggt ttt                           33

<210> SEQ ID NO 14
<211> LENGTH: 33
<212> TYPE: DNA
<213> ORGANISM: Artificial Sequence
<220> FEATURE:
<223> OTHER INFORMATION: PCR primer

<400> SEQUENCE: 14
ctgattacct ccagtatcag catcattgac aat                           33

<210> SEQ ID NO 15
<211> LENGTH: 33
<212> TYPE: DNA
<213> ORGANISM: Artificial Sequence
<220> FEATURE:
<223> OTHER INFORMATION: PCR primer

<400> SEQUENCE: 15
gatactggaa gcagcaatca gaatggttta tta                           33

<210> SEQ ID NO 16
<211> LENGTH: 33
<212> TYPE: DNA
<213> ORGANISM: Artificial Sequence
<220> FEATURE:
<223> OTHER INFORMATION: PCR primer

<400> SEQUENCE: 16
attgctgctt ccagtatcag catcattgac aat                           33

<210> SEQ ID NO 17
<211> LENGTH: 33
<212> TYPE: DNA
<213> ORGANISM: Artificial Sequence
<220> FEATURE:
<223> OTHER INFORMATION: PCR primer

<400> SEQUENCE: 17
actggatgga atcagaatgg tttattaggt ttt                           33

<210> SEQ ID NO 18
<211> LENGTH: 33
<212> TYPE: DNA
<213> ORGANISM: Artificial Sequence
<220> FEATURE:
<223> OTHER INFORMATION: PCR primer

<400> SEQUENCE: 18
ctgattccat ccagtatcag catcattgac aat                           33

<210> SEQ ID NO 19
<211> LENGTH: 33
<212> TYPE: DNA
<213> ORGANISM: Artificial Sequence
<220> FEATURE:
<223> OTHER INFORMATION: PCR primer

<400> SEQUENCE: 19
actggattta atcagaatgg tttattaggt ttt                           33

<210> SEQ ID NO 20
<211> LENGTH: 33
<212> TYPE: DNA
<213> ORGANISM: Artificial Sequence
<220> FEATURE:
<223> OTHER INFORMATION: PCR primer

<400> SEQUENCE: 20
ctgattaaat ccagtatcag catcattgac aat                           33

<210> SEQ ID NO 21
<211> LENGTH: 33
<212> TYPE: DNA
<213> ORGANISM: Artificial Sequence
<220> FEATURE:
<223> OTHER INFORMATION: PCR primer

<400> SEQUENCE: 21
actggagata atcagaatgg tttattaggt ttt                           33

<210> SEQ ID NO 22
<211> LENGTH: 33
<212> TYPE: DNA
<213> ORGANISM: Artificial Sequence
<220> FEATURE:
<223> OTHER INFORMATION: PCR primer

<400> SEQUENCE: 22
ctgattatct ccagtatcag catcattgac aat                33

<210> SEQ ID NO 23
<211> LENGTH: 33
<212> TYPE: DNA
<213> ORGANISM: Artificial Sequence
<220> FEATURE:
<223> OTHER INFORMATION: PCR primer

<400> SEQUENCE: 23
gatactggaa gccataatca gaatggttta tta                33

<210> SEQ ID NO 24
<211> LENGTH: 33
<212> TYPE: DNA
<213> ORGANISM: Artificial Sequence
<220> FEATURE:
<223> OTHER INFORMATION: PCR primer

<400> SEQUENCE: 24
attatggctt ccagtatcag catcattgac aat                33

<210> SEQ ID NO 25
<211> LENGTH: 33
<212> TYPE: DNA
<213> ORGANISM: Artificial Sequence
<220> FEATURE:
<223> OTHER INFORMATION: PCR primer

<400> SEQUENCE: 25
gatactggaa gcttaaatca gaatggttta tta                33

<210> SEQ ID NO 26
<211> LENGTH: 33
<212> TYPE: DNA
<213> ORGANISM: Artificial Sequence
<220> FEATURE:
<223> OTHER INFORMATION: PCR primer

<400> SEQUENCE: 26
atttaagctt ccagtatcag catcattgac aat                33

<210> SEQ ID NO 27
<211> LENGTH: 33
<212> TYPE: DNA
<213> ORGANISM: Artificial Sequence
<220> FEATURE:
<223> OTHER INFORMATION: PCR primer

<400> SEQUENCE: 27
gatactggaa gcgtcaatca gaatggttta tta                33

<210> SEQ ID NO 28
<211> LENGTH: 33
<212> TYPE: DNA
<213> ORGANISM: Artificial Sequence
<220> FEATURE:
<223> OTHER INFORMATION: PCR primer

<400> SEQUENCE: 28
attgacgctt ccagtatcag catcattgac aat                33

<210> SEQ ID NO 29
<211> LENGTH: 33

```
<212> TYPE: DNA
<213> ORGANISM: Artificial Sequence
<220> FEATURE:
<223> OTHER INFORMATION: PCR primer

<400> SEQUENCE: 29
gatactggaa gccaaaatca gaatggttta tta                                  33

<210> SEQ ID NO 30
<211> LENGTH: 33
<212> TYPE: DNA
<213> ORGANISM: Artificial Sequence
<220> FEATURE:
<223> OTHER INFORMATION: PCR primer

<400> SEQUENCE: 30
attttggctt ccagtatcag catcattgac aat                                  33

<210> SEQ ID NO 31
<211> LENGTH: 33
<212> TYPE: DNA
<213> ORGANISM: Artificial Sequence
<220> FEATURE:
<223> OTHER INFORMATION: PCR primer

<400> SEQUENCE: 31
gatactggaa gcgaaaatca gaatggttta tta                                  33

<210> SEQ ID NO 32
<211> LENGTH: 33
<212> TYPE: DNA
<213> ORGANISM: Artificial Sequence
<220> FEATURE:
<223> OTHER INFORMATION: PCR primer

<400> SEQUENCE: 32
attttcgctt ccagtatcag catcattgac aat                                  33

<210> SEQ ID NO 33
<211> LENGTH: 33
<212> TYPE: DNA
<213> ORGANISM: Artificial Sequence
<220> FEATURE:
<223> OTHER INFORMATION: PCR primer

<400> SEQUENCE: 33
gatactggaa gcgataatca gaatggttta tta                                  33

<210> SEQ ID NO 34
<211> LENGTH: 33
<212> TYPE: DNA
<213> ORGANISM: Artificial Sequence
<220> FEATURE:
<223> OTHER INFORMATION: PCR primer

<400> SEQUENCE: 34
attatcgctt ccagtatcag catcattgac aat                                  33

<210> SEQ ID NO 35
<211> LENGTH: 33
<212> TYPE: DNA
<213> ORGANISM: Artificial Sequence
<220> FEATURE:
<223> OTHER INFORMATION: PCR primer

<400> SEQUENCE: 35
```

```
gatactggaa gccctaatca gaatggttta tta                              33
```

<210> SEQ ID NO 36
<211> LENGTH: 33
<212> TYPE: DNA
<213> ORGANISM: Artificial Sequence
<220> FEATURE:
<223> OTHER INFORMATION: PCR primer

<400> SEQUENCE: 36

```
attagggctt ccagtatcag catcattgac aat                              33
```

<210> SEQ ID NO 37
<211> LENGTH: 33
<212> TYPE: DNA
<213> ORGANISM: Artificial Sequence
<220> FEATURE:
<223> OTHER INFORMATION: PCR primer

<400> SEQUENCE: 37

```
gatactggaa gcacaaatca gaatggttta tta                              33
```

<210> SEQ ID NO 38
<211> LENGTH: 33
<212> TYPE: DNA
<213> ORGANISM: Artificial Sequence
<220> FEATURE:
<223> OTHER INFORMATION: PCR primer

<400> SEQUENCE: 38

```
atttgtgctt ccagtatcag catcattgac aat                              33
```

<210> SEQ ID NO 39
<211> LENGTH: 33
<212> TYPE: DNA
<213> ORGANISM: Artificial Sequence
<220> FEATURE:
<223> OTHER INFORMATION: PCR primer

<400> SEQUENCE: 39

```
gatactggaa gcattaatca gaatggttta tta                              33
```

<210> SEQ ID NO 40
<211> LENGTH: 33
<212> TYPE: DNA
<213> ORGANISM: Artificial Sequence
<220> FEATURE:
<223> OTHER INFORMATION: PCR primer

<400> SEQUENCE: 40

```
attaatgctt ccagtatcag catcattgac aat                              33
```

<210> SEQ ID NO 41
<211> LENGTH: 33
<212> TYPE: DNA
<213> ORGANISM: Artificial Sequence
<220> FEATURE:
<223> OTHER INFORMATION: PCR primer

<400> SEQUENCE: 41

```
gatactggaa gcgctaatca gaatggttta tta                              33
```

<210> SEQ ID NO 42
<211> LENGTH: 33
<212> TYPE: DNA
<213> ORGANISM: Artificial Sequence

```
<220> FEATURE:
<223> OTHER INFORMATION: PCR primer

<400> SEQUENCE: 42
attagcgctt ccagtatcag catcattgac aat                                33

<210> SEQ ID NO 43
<211> LENGTH: 33
<212> TYPE: DNA
<213> ORGANISM: Artificial Sequence
<220> FEATURE:
<223> OTHER INFORMATION: PCR primer

<400> SEQUENCE: 43
gatactggaa gctggaatca gaatggttta tta                                33

<210> SEQ ID NO 44
<211> LENGTH: 33
<212> TYPE: DNA
<213> ORGANISM: Artificial Sequence
<220> FEATURE:
<223> OTHER INFORMATION: PCR primer

<400> SEQUENCE: 44
attccagctt ccagtatcag catcattgac aat                                33

<210> SEQ ID NO 45
<211> LENGTH: 33
<212> TYPE: DNA
<213> ORGANISM: Artificial Sequence
<220> FEATURE:
<223> OTHER INFORMATION: PCR primer

<400> SEQUENCE: 45
gatactggaa gcggtaatca gaatggttta tta                                33

<210> SEQ ID NO 46
<211> LENGTH: 33
<212> TYPE: DNA
<213> ORGANISM: Artificial Sequence
<220> FEATURE:
<223> OTHER INFORMATION: PCR primer

<400> SEQUENCE: 46
attaccgctt ccagtatcag catcattgac aat                                33

<210> SEQ ID NO 47
<211> LENGTH: 33
<212> TYPE: DNA
<213> ORGANISM: Artificial Sequence
<220> FEATURE:
<223> OTHER INFORMATION: PCR primer

<400> SEQUENCE: 47
gatactggaa gctttaatca gaatggttta tta                                33

<210> SEQ ID NO 48
<211> LENGTH: 33
<212> TYPE: DNA
<213> ORGANISM: Artificial Sequence
<220> FEATURE:
<223> OTHER INFORMATION: PCR primer

<400> SEQUENCE: 48
attaaagctt ccagtatcag catcattgac aat                                33
```

<210> SEQ ID NO 49
<211> LENGTH: 33
<212> TYPE: DNA
<213> ORGANISM: Artificial Sequence
<220> FEATURE:
<223> OTHER INFORMATION: PCR primer

<400> SEQUENCE: 49
gatactggaa gctataatca gaatggttta tta                33

<210> SEQ ID NO 50
<211> LENGTH: 33
<212> TYPE: DNA
<213> ORGANISM: Artificial Sequence
<220> FEATURE:
<223> OTHER INFORMATION: PCR primer

<400> SEQUENCE: 50
attatagctt ccagtatcag catcattgac aat                33

<210> SEQ ID NO 51
<211> LENGTH: 33
<212> TYPE: DNA
<213> ORGANISM: Artificial Sequence
<220> FEATURE:
<223> OTHER INFORMATION: PCR primer

<400> SEQUENCE: 51
gatactggaa gctgcaatca gaatggttta tta                33

<210> SEQ ID NO 52
<211> LENGTH: 33
<212> TYPE: DNA
<213> ORGANISM: Artificial Sequence
<220> FEATURE:
<223> OTHER INFORMATION: PCR primer

<400> SEQUENCE: 52
attgcagctt ccagtatcag catcattgac aat                33

<210> SEQ ID NO 53
<211> LENGTH: 33
<212> TYPE: DNA
<213> ORGANISM: Artificial Sequence
<220> FEATURE:
<223> OTHER INFORMATION: PCR primer

<400> SEQUENCE: 53
gatactggaa gcatgaatca gaatggttta tta                33

<210> SEQ ID NO 54
<211> LENGTH: 33
<212> TYPE: DNA
<213> ORGANISM: Artificial Sequence
<220> FEATURE:
<223> OTHER INFORMATION: PCR primer

<400> SEQUENCE: 54
attcatgctt ccagtatcag catcattgac aat                33

<210> SEQ ID NO 55
<211> LENGTH: 33
<212> TYPE: DNA
<213> ORGANISM: Artificial Sequence
<220> FEATURE:
<223> OTHER INFORMATION: PCR primer

```
<400> SEQUENCE: 55
gatactggaa gcaaaaatca gaatggttta tta                                   33

<210> SEQ ID NO 56
<211> LENGTH: 33
<212> TYPE: DNA
<213> ORGANISM: Artificial Sequence
<220> FEATURE:
<223> OTHER INFORMATION: PCR primer

<400> SEQUENCE: 56 attttgctt ccagtatcag catcattgac aat                                    33

<210> SEQ ID NO 57
<211> LENGTH: 33
<212> TYPE: DNA
<213> ORGANISM: Artificial Sequence
<220> FEATURE:
<223> OTHER INFORMATION: PCR primer

<400> SEQUENCE: 57
gatactggaa gccgtaatca gaatggttta tta                                   33

<210> SEQ ID NO 58
<211> LENGTH: 33
<212> TYPE: DNA
<213> ORGANISM: Artificial Sequence
<220> FEATURE:
<223> OTHER INFORMATION: PCR primer

<400> SEQUENCE: 58
attacggctt ccagtatcag catcattgac aat                                   33

<210> SEQ ID NO 59
<211> LENGTH: 33
<212> TYPE: DNA
<213> ORGANISM: Artificial Sequence
<220> FEATURE:
<223> OTHER INFORMATION: PCR primer

<400> SEQUENCE: 59
gatactggaa gcaataatca gaatggttta tta                                   33

<210> SEQ ID NO 60
<211> LENGTH: 33
<212> TYPE: DNA
<213> ORGANISM: Artificial Sequence
<220> FEATURE:
<223> OTHER INFORMATION: PCR primer

<400> SEQUENCE: 60
attattgctt ccagtatcag catcattgac aat                                   33
```